United States Patent [19]
Swithenbank et al.

[11] 3,954,875
[45] May 4, 1976

[54] BENZOPHENONE HERBICIDES

[75] Inventors: Colin Swithenbank, Perkasie; Wayne O. Johnson, Warminster, both of Pa.

[73] Assignee: Rohm and Haas Company, Philadelphia, Pa.

[22] Filed: Dec. 26, 1973

[21] Appl. No.: 428,465

[52] U.S. Cl. ............................ 260/591; 424/331; 71/123
[51] Int. Cl.² .................. C07C 49/80; C07C 49/84
[58] Field of Search .................................. 260/591

[56] References Cited
UNITED STATES PATENTS
3,873,304   3/1975   Yamada et al. .................... 260/591

OTHER PUBLICATIONS
Yamada et al., Chem. Abstracts 78 147571f (1973).

*Primary Examiner*—D. Horwitz
*Attorney, Agent, or Firm*—William E. Lambert, III

[57] ABSTRACT

Compounds of the formula

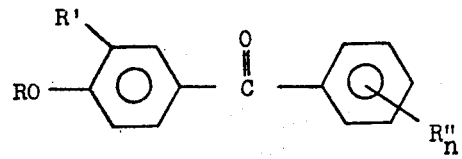

wherein
- R is an alkyl or an allyl group,
- R' is an alkyl group,
- R'' is an alkyl group, an alkoxy group, or a trihaloalkyl group, and
- n is 1 or 2 and compositions containing these compounds exhibit herbicidal activity.

3 Claims, No Drawings

BENZOPHENONE HERBICIDES

This invention relates to novel compounds which show activity as herbicides, to novel herbicidal compositions, and to methods of controlling weeds with the compounds and the herbicidal compositions.

An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known herbicides fall short of these ideals, and it would thus be desirable to have new herbicides which show more selective control of undesirable plants among desirable crop plants or which complement known herbicides in activity.

In accordance with the present invention, there is provided a new class of novel benzophenones having the formula

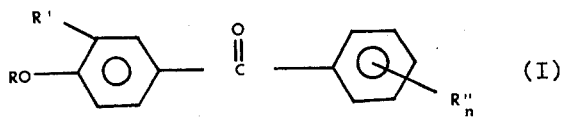

wherein
R is an alkyl group, preferably having 1 to 4 carbon atoms, or an allyl group,
R' is an alkyl group, preferably having 1 to 4 carbon atoms,
R'' is an alkyl group, preferably having 1 to 4 carbon atoms, an alkoxy group, preferably having 1 to 4 carbon atoms, or a trihaloalkyl group, preferably a trifluoromethyl group,
n is an integer of 1 to 2.

The alkyl portion of the alkyl-containing R, R' and R'' substituents can have either a straight- or branched-chain spatial configuration. These novel compounds have been found to show unexpected activity as weed control agents. In a preferred embodiment of the invention, R and R' are methyl groups, R'' is a methyl group or a trifluoromethyl group, most preferably in the 3-position, and $n$ is one.

Examples of the compounds of the invention embraced by Formula I include:
4-methoxy-3,3'-dimethylbenzophenone,
4-methoxy-3,4'-dimethylbenzophenone,
2',4-dimethoxy-3-methylbenzophenone,
4-ethoxy-2',3-dimethylbenzophenone,
4-ethoxy-2'-methoxy-3-methylbenzophenone,
4-ethoxy-3,3'5'-trimethylbenzophenone,
3,3'-dimethyl-4-i-propoxylbenzophenone,
4-methoxy-3-methyl-3'-trifluoromethylbenzophenone,
3-methyl-4-i-propoxy-3'-trifluoromethylbenzophenone,
4-ethoxy-3-methyl-4'-trifluoromethylbenzophenone,
4-allyloxy-3,3'-dimethylbenzophenone,
4-allyloxy-3-methyl-3'-trifluoromethylbenzophenone, and the like.

The novel benzophenones of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period. The benzophenones of the invention are generally preferred in preemergence applications.

Among the crops on which the benzophenones of the invention can be advantageously employed to give selective control of weeds are, for example, rice, wheat, barley, corn, soybeans, cotton, and peanuts.

The compounds of the invention are useful for controlling weeds in rice crops. When used in transplanted rice crops, the compounds can be applied either preemergence or postemergence to the weeds — that is, they can be applied to the transplanted rice plants and their growth medium either before the weed plants have emerged or while they are in their early stages of growth. The compounds can be applied to the growth medium either before or after the rice has been transplanted to or emerged from that medium.

The compounds of the invention can be applied in any amount which will give the required control of weeds. A preferred rate of application of the herbicides of the invention is from about ¼ to about 20 pounds, and most preferably about ½ to about 10 pounds, of the compound per acre.

A benzophenone of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to disolve, disperse, or diffuse a herbicidal compound in the composition without impairing the effectiveness of the herbicidal compound and which by itself has no detrimental effect of the soil, equipment, crops, or agronomic environment. Mixtures of the compounds of the invention may also be used in any of these herbicidal formulations. The herbicidal compositions of the invention can be either solid or liquid formulations or solutions. For example, compounds can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include alcohols, ketones, aromatic hydrocarbons, dimethylformamide, dioxane, dimethyl sulfoxide, and the like. Mixtures of these solvents can also be used. The concentration of the solution can vary from about 2 to about 98% with a preferred range being about 25 to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10 to 60% and in flowable emulsion concentrates, this can be as high as about 75%.

Wettable powders suitable for spraying can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20 to 98%, preferably about 40 to 75%. A dispersing agent can constitute about 0.5 to about 3% of the composition, and a wetting agent can constitute from about 0.1 to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient methods of preparing a dust is to dilute a wettable powder with a finely divided carrier. Dust concentrates containing about 20 to 80% of the active ingredient are commonly made and are subsequently diluted to about 1 to 10% use concentration.

Granular formulations can be prepared by impregnating a solid such as granular fuller's earth, vermiculite, ground corn cobs, seed hulls, including bran or other grain-hulls, or similar material. A solution of one or more of the benzophenones in a volatile organic solvent can be sprayed or mixed with the granular solid and the solvent then removed by evaporation. The granular material can be any suitable size, with a preferable size range of 16 to 60 mesh. The active compound will usually comprise about 2 to 15% of the granular formulation.

The compounds of the invention can also be mixed with fertilizers or fertilizing materials before their application. In one type of solid fertilizing composition in which the compounds can be used, particles of a fertilizer or fertilizing ingredients, such as ammonium sulfate, ammonium nitrate, or ammonium phosphate, can be coated with one or more of the compounds. The solid compounds and solid fertilizing materials can also be admixed in mixing or blending equipment, or they can be incorporated with fertilizers in granular formulations. Any relative proportion of benzophenone and fertilizer can be used which is suitable for the crops and weeds to be treated. The benzophenone will commonly be from about 5 to about 25% of the fertilizing composition. The compositions provide fertilizing materials which promote the rapid growth of desired plants, and at the same time control the growth of undesired plants.

The compounds of the invention can be applied as herbicidal sprays by methods commonly employed, such as conventional high-gallonage hydraulic sprays, low-gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with the compounds of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di(n-propyl)thiocarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-ethoxy-4'-nitrodiphenyl ether
2-chloro-4-trifluoromethyl-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)-chloroacetamide
N-n-methoxymethyl-N-(2,6-diethylphenyl)-chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)2,6-dinotro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazine-(4)3H-one-2,2-diozide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The benzophenones of the method can be prepared by several known general synthetic routes. One useful procedure involves reacting a 3-alkyl-4-alkoxybenzene with a suitably substituted benzoic acid chloride using carbon disulfide or ethylene dichloride as a solvent and aluminum chloride as a catalyst. Generally, this reaction is carried out at a temperature of about 20° to about 70°C, using approximately equimolar amounts of the starting reactants. Other useful solvents include nitrobenzene, nitromethane, chloroform, methylene chloride, and the like. Another useful procedure involves reacting a 3-alkyl-4-alkoxybenzene with a suitably substituted benzoic acid in the presence of polyphosphoric acid. Generally, this reaction is carried out at a temperature of about 40° to about 120°C, also using approximately equimolar amounts of the starting reactants. Additional solvent is usually necessary. Variations of other known processes for preparing benzophenones can also be used to prepare the compounds of the invention.

The following examples will further illustrate this invention but are not intended to limit it in any way. In Table I, typical benzophenones of the invention are listed with their melting points and elemental analyses. Specific, illustrative preparations of the compounds of Examples 1, 2, 3 and 4 are described after Table I.

TABLE I

Benzophenones - Physical Data

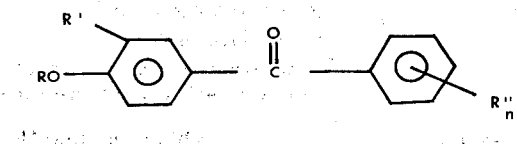

| Example No. | R | R' | R"ₙ | M.P. (°C) | Empirical Formula | | %C | %H | %F |
|---|---|---|---|---|---|---|---|---|---|
| 1 | $CH_3$ | $CH_3$ | 3-$CF_3$ | 56–9 | $C_{16}H_{13}F_3O_2$ | found | 65.47 | 4.60 | 19.93 |
|   |   |   |   |   |   | theory | 65.30 | 4.45 | 19.36 |
| 2 | $CH_3$ | $CH_3$ | 3-$CH_3$ | 64–6 | $C_{16}H_{16}O_2$ | found | 79.96 | 6.83 | — |
|   |   |   |   |   |   | theory | 79.97 | 6.71 | — |
| 3 | $CH_3$ | $CH_3$ | 2-$CH_3$ | 72–3 | $C_{16}H_{16}O$ | found | 79.96 | 6.83 | — |
|   |   |   |   |   |   | theory | 79.97 | 6.71 | — |
| 4 | $CH_3$ | $CH_3$ | 4-$CH_3$ | 75–7 | $C_{16}H_{16}O_2$ | found | 80.18 | 6.41 | — |
|   |   |   |   |   |   | theory | 79.97 | 6.71 | — |
| 5 | $CH_3$ | $CH_3$ | 3,5-$(CH_3)_2$ | 84–5.5 | $C_{17}H_{18}O_2$ | found | 79.96 | 6.95 | — |
|   |   |   |   |   |   | theory | 80.26 | 7.12 | — |
| 6 | $CH_3$ | $CH_3$ | 2-$OCH_3$ | 67–8 | $C_{16}H_{16}O_3$ | found | 74.69 | 6.49 | — |
|   |   |   |   |   |   | theory | 74.95 | 6.30 | — |
| 7 | $CH_3$ | $CH_3$ | 3-$OCH_3$ | 53–4 | $C_{16}H_{16}O_3$ | found | 74.34 | 6.47 | — |
|   |   |   |   |   |   | theory | 74.95 | 6.30 | — |
| 7a | $CH_3$ | $CH_3$ | 4-$OCH_3$ | 61–3 | $C_{16}H_{16}O_3$ | found | 74.89 | 6.56 | — |
|   |   |   |   |   |   | theory | 74.95 | 6.30 | — |

EXAMPLE 1

Preparation of 4-methoxy-3-methyl-3'-trifluoromethylbenzophenone m-Trifluoromethylbenzoic acid (19.0g, 0.10 mole) and o-methylanisole (12.2g, 0.10 mole) are combined in 50 ml of polyphosphoric acid (PPA) and warmed with stirring to 90°C for 4.5 hours. The cooled reaction mixture is then poured into ice water and extracted into ethyl acetate (200 ml) to give, after extraction with 5% aqueous sodium hydroxide 15 g of product (53%), m.p. 56°–59°C, upon removal of the solvent in vacuo.

EXAMPLE 2

Preparation of 4-methoxy-3,3'-dimethylbenzophenone m-Toluic acid (13.6 g, 0.10 mole) and o-methylanisole (12.2 g, 0.10 mole) are combined in 50 ml of polyphosphoric acid (PPA) and warmed with stirring to 80°C for 2 hours. The cooled reaction mixture is then poured into ice water and extracted into ethyl acetate (200 ml) and washed with 5% sodium hydroxide to give 14.4 g of product (60%), m.p. 62°–4°C, upon removal of the solvent in vacuo.

EXAMPLE 3

Preparation of 4-methoxy-2',3-dimethylbenzophenone o-Toluoyl chloride (15.4 g, 0.10 mole) and o-methylanisole (12.2 g, 0.10 mole) are combined in 50 ml of polyphosphoric acid (PPA) and warmed with stirring on a steam bath for 2–3 days. The cooled reaction mixture is then poured into water and extracted into benzene, dried (anhydrous $MgSO_4$) and the solvent removed in vacuo to give 7.5 g of product (31%), m.p. 72°–73°C.

EXAMPLE 4

Preparation of 4-methoxy-3,4'-dimethylbenzophenone p-Toluoyl chloride (15.5g, 0.10 mole) is added dropwise at room temperature over a 1 hour period to a mixture of o-methylanisole (15.3 g, 0.125 mole) and aluminum chloride ($AlCl_3$, 37.3g, 0.28 mole) in carbon disulfide ($CS_2$, 50 ml) in a flask fitted with a stirrer, addition funnel, drying tube and reflux condenser. The reaction mixture is then refluxed for 1 hour, cooled and the carbon disulfide removed in vacuo. The residue is then slurried in methylene chloride and poured into 400 g of cracked ice containing 20 ml of concentrated hydrochloric acid. This mixture is then transferred to a separatory funnel and extracted with additional methylene chloride (3 × 15 ml) and the methylene chloride extract dried (anhydrous $MgSO_4$) prior to concentrating in vacuo. The residue was then triturated with benzene. The benzene extract is then diluted with hexane which results in precipitation of 2.5 g. of product (10%), m.p. 73°–5°C.

EXAMPLES 8 – 13

Following the procedures of Examples 1 to 7, other benzophenones of Formula I are prepared. Among the compounds of the invention which are prepared by these procedures are:

4-ethoxy-3,3'-dimethylbenzophenone,
4-methoxy-3-methyl-4'-trifluoroethylbenzophenone,
4-ethoxy-3-methyl-3'-trifluoromethylbenzophenone,
4-allyloxy-3,3'-dimethylbenzophenone,
4-t-butoxy-3-methyl-3'-trifluoromethylbenzophenone, and
3,3'-dimethyl-4-i-propoxybenzophenone.

EXAMPLE 14

This example shows the use of compounds of the invention in controlling a number of common weeds of preemergence application. Using the procedure described below, the benzophenones of Examples 1 and 2 were evaluated for control of the following weeds:

| | |
|---|---|
| Barnyardgrass | (Echinochloa crusgalli) |
| Crabgrass | (Digitaria spp.) |
| Foxtail | (Setaria italica) |
| Johnsongrass | (Sorghum halepense) |
| Quackgrass | (Agropyron repens) |
| Ryegrass | (Lolium spp.) |
| Yellow millet | (Panicum miliaceaum) |
| Wild oats | (Sesbania spp.) |
| Coffeeweed | (Sesbania spp.) |
| velvetleaf | (Abutilon theophrasti) |

The following test procedure is employed. Seeds of selected weeds are planted in soil in flats, and the flats are treated with the test compound immediately after the planting. The compound to be evaluated is dissolved in acetone, diluted with water, and sprayed over the flats using a carrier volume equivalent to 50 gallons per acre at the rate of application (pounds per acre, lb/A.) specified in the tables. About 2 weeks after the application of the test compound, the state of growth of the plants is observed and the phytotoxic effect of the compound is evaluated. Table II gives the average percent control achieved by the test compounds in terms of the percent of the plants which are killed by the compounds.

TABLE II

HERBICIDAL ACTIVITY
(% control)

| Compound of Example No. | Rate (lb./A.) | % Control Monocots | Dicots |
|---|---|---|---|
| 1 | 2 | 91 | 65 |
|  | 4 | 97 | 70 |
|  | 8 | 99 | 85 |
| 2 | 2 | 88 | 60 |
|  | 4 | 93 | 55 |
|  | 8 | 100 | 65 |

It is to be understood that changes and variations may be made without departing from the spirit and scope of the invention as defined by the appended claims.

We claim:
1. A compound of the formula

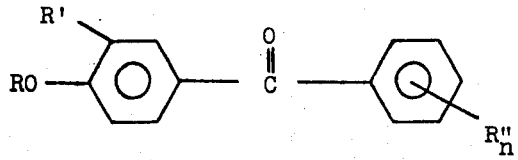

wherein
R is a $(C_1-C_4)$ alkyl group or an allyl group,
R' is a $(C_1-C_4)$ alkyl group,
R'' is a $(C_1-C_4)$ alkoxy group, or a trifluoromethyl group, and
$n$ is 1 or 2.
2. The compound of claim 1 wherein R'' is a trifluoromethyl group and $n$ is 1.
3. The compound of claim 2 wherein R'' is a 3-trifluoromethyl group.

* * * * *

UNITED STATES PATENT AND TRADEMARK OFFICE
CERTIFICATE OF CORRECTION

PATENT NO. : 3,954,875
DATED : May 4, 1976
INVENTOR(S) : Colin Swithenbank and Wayne O. Johnson It is certified that error appears in the above-identified patent and that said Letters Patent are hereby corrected as shown below:

In column 2, line 47, "of" should be --on--.

In column 3, line 47, "methods" should be --method--.

In column 8, line 47, "trifluoroethylbenzophenone" should be --trifluoromethylbenzophenone--.

Signed and Sealed this

Third Day of August 1976

[SEAL]

Attest:

RUTH C. MASON
Attesting Officer

C. MARSHALL DANN
Commissioner of Patents and Trademarks